United States Patent [19]

Carlson

[11] Patent Number: 4,834,789

[45] Date of Patent: May 30, 1989

[54] PROCESS FOR TREATING PLANTS

[75] Inventor: Danis R. Carlson, Blaine, Minn.

[73] Assignee: Dan Carlson Scientific Enterprises, Inc., Blaine, Minn.

[21] Appl. No.: 76,046

[22] Filed: Jul. 21, 1987

Related U.S. Application Data

[63] Continuation-in-part of Ser. No. 802,477, Nov. 27, 1985, Pat. No. 4,680,889, which is a continuation of Ser. No. 792,617, Oct. 22, 1985, abandoned, which is a continuation of Ser. No. 518,008, Jul. 28, 1983, abandoned, which is a continuation of Ser. No. 286,260, Jul. 23, 1981, abandoned.

[51] Int. Cl.$^4$ ............................................. A01N 37/38
[52] U.S. Cl. ........................................ 71/117; 71/88; 71/92; 71/93; 71/86; 71/100; 71/105; 71/115; 71/121; 71/120; 71/109; 71/118; 47/58
[58] Field of Search ........................................ 71/1, 117

[56] References Cited

U.S. PATENT DOCUMENTS

| | | | |
|---|---|---|---|
| Re. 23,115 | 5/1949 | Lontz | 71/117 |
| 2,450,543 | 10/1948 | Flenner | 71/117 |
| 2,515,198 | 7/1950 | Dosser et al. | 71/117 |
| 2,519,780 | 8/1950 | Morrill | 71/117 |
| 4,680,889 | 7/1987 | Carlson | 71/89 |

Primary Examiner—Glennon H. Hollrah
Assistant Examiner—A. A. Owens
Attorney, Agent, or Firm—Merchant, Gould, Smith, Edell, Welter & Schmidt

[57] ABSTRACT

The present invention provides a method for controlling weed, e.g. plant growth, using a combination of an herbicide that is absorbed by the plant, together with the application of sound at a frequency of between 4 and 6 kilohertz at a volume of about 115 decibels to facilitate the uptake of the herbicide by the plant.

15 Claims, No Drawings

PROCESS FOR TREATING PLANTS

BACKGROUND OF THE INVENTION

This is a Continuation-in-Part Application of U.S. Patent Application Ser. No. 802,477 filed Nov. 27, 1985; which is a continuation of U.S. Patent Application Ser. No. 792,617 filed Oct. 22, 1985; which is a continuation of U.S. Patent Application Ser. No. 518,008 filed July 28, 1983; which is a continuation of U.S. Patent Application Ser. No. 286,260 filed July 23, 1981.

The present invention relates to a process for affecting plant growth and, more particularly, to stimulating plant growth by subjecting the plant to sound waves. The present invention further includes use of sound waves to assist in the assimilation of growth inhibiting solutions by plants. For example, one may decrease the level of herbicide needed to provide an effective killing dosage, thus minimizing pollution.

History reveals that many eforts have been made to affect growth rates in plants. This effort has generally been made to increase the food production from plants. For example, hybridizing has increased in a major way the yield obtained from such crops as corn, wheat, tomatoes, carrots and the like. Other efforts have been made in the development and use of plant foods and fertilizers. In some instances, fertilizer has been injected into the soil along with seed at the time of planting. It has also been known to spray fertilizer onto growing plants to feed systemically through the leaves.

More recently, effort has been directed toward hormone treatment of plants using sound and gibberellin or gibberellic acid. See. U.S. Pat. No. 4,680,889. It is recognized that gibberellin produces increased growth rates and increased plant sizes. There are nine types of gibberellin identified to date. Five of the gibberellins have been isolated from fungi such as *Phaseolus Multiflorus.* Three of the gibberellins has been isolated from higher plants, and one of the gibberellins has been isolated from both fungi and higher plants. The nine gibberellins have been designated types A-1 through A-9. The gibberellins are native plant growth hormones.

Sound waves have previously been used on plants to promote the growth and health of plants. A description of such use is found in the book entitled, "The Secret Life of Plants," written by Peter Thompkins and Christopher Bird and published by Harper and Row in 1973. The chapter entitled "The Harmonic Life of Plants" is of particular interest.

SUMMARY OF THE PRESENT INVENTION

The present invention is a process for treating plants with sound of a particular frequency to stimulate growth.

Further the present invention is a process of treating plants with such sound to force osmosis of growth affecting herbicide compositions into the plants. The process may include the steps of applying the growth affecting composition to the plant and subjecting the plant to sound waves while the composition is disposed on said plant. Alternatively, herbicide compositions may be applied by spraying during the application of sound. A suitable composition may be an aqueous solution of what is commonly referred to as 2,4D. Detergent may be included in the solution to facilitate uniform distribution of the aqueous solution on the foliage of the plant.

The sound used in the present invention may be produced using any of a variety of mechanisms. One technique that has proven suitable is the use of a recording, e.g. disc recordings and cassette recordings. Alternatively, electronic sound producing devices may be used.

DETAILED DESCRIPTION OF THE PRESENT INVENTION

In one embodiment of the present invention, plants are treated with sound waves desirably in the range of about 4 to 6 kilohertz. In another embodiment of the present invention the plants are treated with a combination of such sound and herbicide chemicals. Any technique may be used to apply the chemicals to the plants. In the case of applying chemicals as an aqueous solution to the foliage of plants, conventional spraying techniques may be used. In the case of applying the chemicals to seeds, the seeds may be wetted with an aqueous solution.

The plant is subjected to sound waves of high frequency. The sound waves may be produced in any manner, for example, sound recordings or sound generating devices. The sound may be of a frequency of 4 to 6 kilohertz, preferably 4.7 to 5.3 kilohertz. The sound waves may be of a constant frequency; however, use of a variable frequency within this range is preferred. For example, the plants may be subjected to sound waves which vary in frequency from 4.7 to 5.3 kilohertz. The period of one rise and fall in frequency may be from 0.1 to 0.5 seconds. The sound may be pulsating, e.g., discontinuous. Sound waves outside this frequency may also be present.

It is believed the sound waves serve to open the individual plant cells to increase the osmotic movement of chemicals into the plant cells. The volume of the sound waves in the present invention may be at least 115 decibels, preferably 115 to 120 decibels at the point where the sound interfaces with the plant foliage, e.g. plant cells. The duration of sound treatment is at least 15 seconds, preferably about 30 seconds to 30 minutes.

The present process for growth promotion has been found suitable for use on ornamentals, vegetables, fruits and the like. The following are illustrative of various plants suitable for growth promotion treatment under the present process:

soybeans, corn, sunflowers, dry edible beans, alfalfa, tomatoes, peppers, cucumbers, lettuce, zucchini, carrots, squash, roses, African violets, orchids, moss roses, purple passion, Boston ivy, English ivy, Hawaiian mylee, flowering shrubs, snowball bushes, fruit trees, weeping willows, silver maples, apples, bananas, oranges, aloe vera, jojoba, guayule, Jerusalem artichokes, Macadamia nut trees leafy vines, flowers or plants normally grown indoors in pots; shrubs, bushes, flowers and ornamentals, orchids, lilies, and other tropical ornamental and vegetable or farm crops.

The present process for growth promotion in most instances produces an increase in growth rate of at least 15 percent and in some instances has resulted in a plant size increase of over five hundred fold. Seed production has been increased by two to three hundred percent and more. The seeds are larger than normal and carry forward the increased production and growth rates. The treated plants have a greater resistance to drought and frost. In some instances, the plant foliage may be treated; in other instances, the roots; and in still others, the seeds are treated prior to germination. Cuttings may be rooted in a solution according to the present invention while sound is applied.

The present process for growth eradication has been found suitable for any undesirable plant growth such as grasses, rag weed, button weed and the like. The present process for plant life inhibition may be carried out using any herbicide together with the sound treatment. For example, a conventional weed spray such as 2,4D may be used. The herbicide may be used at a lower level of application and acts more rapidly than conventional use. For example, the herbicide concentration and thus application may be reduced by 5 to 75 percent. Alternatively, the herbicide may be maintained at full strength and have a more potent effect than was the case heretofore.

Depending upon the situation, any particular plant may be considered to be a weed. In a watermelon patch, volunteer tomatoe plants are weeds. In an apple orchard, maple saplings are weeds. Thus, the present invention contemplates use of the process on any plant growth that is undesired. Certain plants are well recognized as weeds and as being undesired. Perhaps this is because such plants are common infestations to many cultivated crops. These common weeds are often tenacious and very difficult to eliminate from the crop. Such weeds are often difficult to kill. Use of herbicides has been under attack in recent years for environmental reasons. With the present process the killing dosage of herbicide is significantly reduced, thus reducing the environmental impact. The present process can also make such herbicides effective on plants where the herbicide has had a marginal effect in the past.

Illustrative of the weeds that may be treated according to the present invention are Canadian thistle, quackgrass, yellow nutsedge, bluegrass, sowthistle, field bindweed, leafy spurge, common milkweed, wirestem muhly, perennial buttercups, germander, bull thistle, cockleburr, chickweed, goldenrod, pigweed, mustards, burdoch, button weed, wild sunflowers, ash, wild blackberry, hawthorne, oak, ivy, sumac, maple, willow, chokeberry, poison ivy, mesquite, brambles, wild grape, honeysuckle, alder, pine, fir, spruce, rag weed, pokeberry, yucca, smartweed, clovers, knotweed, shepherd's purse, crabgrass, foxtail, coffeeweed, teaweed, kochia, velvetleaf, cockles, knapweed, dock, gooseweed, toadflax, johnsongrass, dandelions, sandburr, groundcherry, morningglory, beggarweed, annual bluegrass, fiddleneck, tarweed, speedwell, shattercane and the like.

The present process contemplates use of any plant herbicide that functions through the chemical take up by the plant, such herbicide being used together with the application of sound to the plant. The composition may be a member of the group consisting of phenoxy compounds, benzoic acid derivatives, acedic acid derivatives, phthallic acid derivatives, dintro analines, nitrites, admides, acetamides, anilides, carbamates, heterocyclic nitrogen derivatives, urea compounds, metal organics and metal inorganics. The more recognized herbicides include such commercial products as 2,4-D, Bladex TM (cyanazine), Eradicane TM (EPTC and dichormid), Lasso-Atrazine TM (alachlor and atrazine), and Roundup TM (glyphosate). The herbicide may be any of a wide variety of compositions having herbicidal properties. Illustrative of commercially available herbicides suitable for the present invention include the following: Amiben TM (e.g. chloramben), Antor TM (e.g. diethatyl), Avenge TM (e.g. atrazine and difenzoquate), Balan TM , (e.g. benefin), Banvel TM (e.g. dicamba), Basagran TM (e.g. bentazon), Basalin TM (e.g. fluchloralin), Betamix TM (e.g. desmedipham and phenmedipham), Bicap TM (e.g. atrazine and metochlor), Bladex TM (e.g. cyanazine), Blazer TM (e.g. acifluorfen), Brominal TM (e.g. bromoxynil), Bronate TM (e.g. bromoxynil and MCPA), Bronco TM (e.g. alachlor and glyphosate), Buctril TM (e.g. bromoxynil), Butoxone TM (e.g. 2,4-DB), Carbyne 2EC TM (e.g. barban), Classic TM (e.g. DPX-F6025), Command TM (e.g. FMC-57027), Conquest TM (e.g. cyanazine and atrazine), Dowpon M TM (e.g. 2,4-D amine, 2,4-D ester and dalapon), Dual TM (e.g. matachlor), Eptam TM (e.g. EPTC), Eradicane TM (e.g. EPTC and dichlormid), Far-Go TM (e.g. triallate), Fusilade 2000 TM (e.g. fluazifop-P), Genate Plus TM (e.g. butylate and dichlormid), Gramoxone Super TM (e.g. paraquat), Herbicide 273 TM (e.g. endothall), Hoelon TM (e.g. diclofop), Kerb TM (e.g. pronamide), Laddock TM (e.g. bentazon and atrazine), Lasso TM (e.g. alachlor), Lexone TM (e.g. metribuzin), Lorox TM (e.g. linuron), Marksman TM (e.g. dicamba and atrazine), Modown TM (e.g. MCPA amine, MCPA ester and bifenox), One-Shot TM (e.g. dichiofop, bromoxinil and MCPA), and Tandum TM (e.g. tridiphane).

Post-emergence application of 2,4-D has been the major herbicide practice on broadleaf perennials for more than 30 years. The designation "2,4-D" is the common term referring to 2,4-dichlorophenoxyacetic acid. This herbicide is also used as its salts, e.g. sodium, ammonium, amine or esters. 2,4-D is particularly effective in the present invention for treatment of bindweed, Canadian thistle, chickweed, cockleburr, goldenrod, ivy, hoary cress, jimsonweed, lambsquarters, locoweed, mustards, pigweed, plantain, Russian thistle, purslane, sunflower, and willows. The present combination of herbicide and sound treatment makes 2,4-D more effective than it has ever been in the past and yet permits use of smaller amounts of the herbicide. Other suitable herbicides for use in the present invention include Dicamba TM (e.g. 3,6-dichloro-0-anisic acid), Ioxynil TM (e.g. 4-hydroxy 3,5-diiodobenzonitrile), and Pyrazon TM (e.g. 5-amino-4-chloro-2-phenyl-3 (2H)-pyridazinone).

Another herbicide that is particularly suitable for use in the present invention is 2,4-DP or more properly identified as 2,4-dichlorophenoxypropionic acid. This herbicide is useful in the present invention to control woody plants, e.g. trees, bushes, vines and the like. A commercial product using this herbicide is known as Weedone 2,4-DP TM . Other herbicides suitable for use in the present invention on such woody plants are 2,4-dichorophenoxypropionic acid, ammonium sulfamate, (aminocarbonyl) phosphonic acid, and 3,5,6-trichloro-2-pyridyl-oxyacetic acid. These herbicides are most useful to inhibit the growth and life of such plants as elm, cherry, hawthorne, oak, ivy, pine, chokecherry, mesquite, birch, brambles, wild grape, honeysuckle, poison ivy, sumac, yucca, fir, spruce, alder, sandsage, brambles, and willow.

The present invention may be carried out with respect to grasses using such products as CME 127 TM (e.g. 2-chloro-6-nitro-3-phenoxy-aniline), Dyanap TM , Endothall TM (e.g. 7-oxabicyclo (2,2,1) heptane-2,3-dicarboxylic acid), Ethalfluralin TM (e.g. N-ethyl-N-(2-methyl-2-propenyl)-2,6 dinitro-4-(trifluoromethyl) benzenamine), Propanil TM (e.g. 3,4-dichloropropionanilde), CIPC TM (e.g. isopropyl-m-chloro-carbanilate), IPC TM (e.g. ispropoyl-carbanilate), Carbyne ™ (e.g. 4-chloro-2-butynyl m-chlorocarbanilate) and Quinclorac ™ (e.g. 3,7-dichloro-8-quinoline carboxylic acid).

Where specific herbicides have been suggested here, it is to be recognized that a wide variety of other herbicides may be used in the present invention. For example, the various herbicides listed in the book *Agricultural Chemicals,* Book II, Herbicides, 1986-87, revision by W. T. Thomson, are deemed suitable and incorporated by reference. The various herbicides listed in the Thomson book may be used in amounts well reduced from that suggested by Thomson, for example, at a level of from 95 to 25 percent of those set forth in Thomson. Also, it is to be recognized that the usage of the herbicide may be at full recommended level or even higher to result in herbicidal activity well beyond that previously obtained with the particular herbicide.

EXAMPLE 1

(Purple Passion Plant)

The present invention was carried out by treating a purple passion plant with sound. Potting soil was prepared by mixing 45 percent commercially available African Violet potting soil, 45 percent general potting soil (Woolworth's Black Magic ®), 4 percent sheep manure and 1 percent lime. This mixture was placed in a flower pot which had the lower portion filled with charcoal pieces. A small purple passion plant was purchased at a variety store and planted in the potting soil mixture. Sound was applied by playing a recording to produce high frequency sound in the range of between 4 and 6 kilohertz. The sound was at a volume of about 115 decibels and was applied for over 30 seconds. Excellent results were obtained.

EXAMPLE II (Edible Yellow #2 Beans)

A fifty acre field of yellow #2 beans located in Northern Minnesota was treated according to the present invention. Fifty acres of beans were treated using a tractor equipped with an emitting device. The tractor carried a speaker which emitted sound at 4.82 kilohertz per second at a volume of 115 decibels. Sound was applied to the plant as the tractor moved through the field for approximately 3½ hours. Satisfactory results were obtained.

EXAMPLE III (Weeping Willow Tree)

A weeping willow tree was treated according to the present invention. The tree was five feet tall and had a trunk diameter of ¼ inch at the time of planting and commencement of treatment. The tree was treated with sound on a monthly basis. The frequency was between 4 and 6 kilohertz and the sound volume was about 115 decibels. Satisfactory results were obtained.

EXAMPLE IV (Weeping Willow Seedlings)

The process of the present invention was carried out on weeping willow seedlings. The seedlings were obtained as bare-root seedlings. All seedlings were planted in comparable soil and grown for one year without special treatment. The seedlings were equal in size after the year's growth. The seedlings were identified into three test groups, e.g. Groups A, B, and C. Group A was retained as a control and did not receive special treatment during the second year. Group B was grown under conditions identical to Group A except Group B received treatment. More specifically, the seedlings of Group B were treated with sound at a frequency of about 5 kilohertz at a volume of 115 decibels. While receiving the sound treatment, the seedlings of Group B were sprayed with a chemical solution made up from a concentrate. The concentrate included by weight 7.78 percent gibberellin A-3, 7.78 percent surfactant (Basic H ®), 7.78 percent Willard Water, 26.67 percent amino acid and 50 percent seaweed extract. The concentrate was diluted by mixing one fluid ounce of concentrate in one gallon of water. The solution was applied to Group B by wetting the leaves with solution and applying the sound treatment. The sound treatment continued for 30 minutes after the solution was applied to each seedling. The seedlings of Group C were grown in a manner identical to Group B except those seedlings only received the sound treatment and did not receive the chemical application. The new growth, over the summer, was measured with random selection of ten branches from each group. The average annual growth of the branches in each group was as follows: Group A was 41 inches; Group B was 80 inches; and Group C was 45 inches.

EXAMPLE V (Tomato Seedlings)

The present process was applied to tomato seedlings of the type Burpee Big Boy ™. Treated plant growth and production was compared with a control that received no special treatment. A sufficient number of plants were included in control groups. The seedlings were planted on May 1st. The beginning plant sizes were equal in the two groups and the ambient growing conditions were the same for both groups. The treated group was subjected to sound treatment for about ten minutes. The sound was at a frequency of 4 to 6 kilohertz and at a volume of 115 decibels. The treated group grew more rapidly than the untreated group.

EXAMPLE VI (Boston Ivy)

The present process was applied to a Boston Ivy plant which only received sound treatment. The plant was 2 feet in length at commencement of the test on May 1, 1982. The treated plant received the same sound application of 10 minutes on six mornings between June 10, 1982 and September 2, 1982. On Oct. 22 the plant treated with sound was 19 feet 9 inches in length, and the control plant was 12 feet 10 inches in length.

EXAMPLE VII (Jerusalem Artichokes)

Jerusalem artichokes of the variety Mammoth French White ™ were treated according to the present invention and compared with a nontreated control group. All specimens were planted on the first day of May. The treated group was treated by application of sound at a frequency of between 4 and 6 kilohertz for ten minutes six mornings between June 10, 1982 and Sept. 2, 1982.

EXAMPLE VIII (Cherry Tomatoes)

The effect of the use of sound in the present invention was tested by selecting nine uniform cherry tomato plants. The plants were each six inches in height. The plants were divided into three groups of three plants each. Group 1 was treated with the solution described in Example I by spotting 50 microliters of solution over an area of 2.0 square centimeters on the second leaf from the top of the plant. The solution had been labeled with $Fe^{-59}$ isotope. The plants were subjected to 20 mv energy of sound for 15 minutes prior to application of the solution and for 15 minutes following such application. The sound was at between 4 and 6 kilohertz. Group 2 was treated in an identical manner except the sound treatment was omitted. The plants were held for 24 hours. Then a portion of the stem immediately above the treated leaf was removed from each plant in Group 1. The corrected counts per minute per milligram was $2.47 \pm 0.4$. The stem portion immediately beneath the leaf was taken. The corrected counts per minute per milligram was $2.5 \pm 0.17$. Group 2 plants were similarly analyzed. The corresponding values were $0.4 \pm 0.1$ and $1.13 \pm 0.42$ respectively. This shows a substantial effect in chemical uptake by the plants treated with sound over those not treated with sound.

EXAMPLE IX

The present invention was carried out to compare the effect of the chemical application with and without sound application. A control without either chemical or sound was also carried out. Such testing was carried out by applying the composition described in Example I. The plants in each instance were grown from the Punch N' Grow TM product of Northrup King obtained from a commercial source. All plants emerged after one week. The various plants and groups were treated identically except for the fact that Group 1 was a control and did not receive either sound or chemical application. Group 2 received both sound and spray as described in Example IV. The sound, however, was applied by a cassette recording played by a cassette player. The spray was applied by a hand-held spray gun. The sound was applied to the emerged plants for 1/2 hour three times a week. The chemical spray was applied once a week during one of the sound applications. Group 3 received the spray but no sound and Group 4 received sound but no spray. In all instances Groups 2-4 provided more rapid growth than did Group 1. The combination of sound and spray provided greater growth than did either the spray alone or the sound alone. All Groups were started on February 26 and completed on March 19 for a total growth period of 21 days.

EXAMPLE X

A comparative test was carried out as described in Example IX except that started plants of Oak Leaf Ivy were treated. The results of the 21 days growing period were as follows:

| Group | Oak Leaf Ivy Height (cm) | |
|---|---|---|
| | Start | Final |
| 1 | 13.5 | 16.0 |
| 2 | 15.0 | 19.0 |
| 3 | 13.0 | 15.0 |
| 4 | 15.0 | 18.0 |

The plants were again measured after 93 days. The results were as follows:

| Group | Oak Leaf Ivy | |
|---|---|---|
| | Start | Final |
| 1 | 13.5 | 28.0 |
| 2 | 15.0 | 35.0 |
| 3 | 13.0 | 26.5 |
| 4 | 15.0 | 30.0 |

Group 1 — no sound & no spray
2 — sound & spray
3 — spray no sound
4 — sound no spray

EXAMPLE XI

The present invention was carried out on the following plants substantially as described in Example I comparing the present test specimen with controls which did not receive either sound or chemical. The sound was applied for at least 30 minutes.

EXAMPLE XII

Tests were conducted using radioactive isotope $Fe^{59}$ to compare the takeup rate of the growth chemical solution of Example I with and without sound treatment. Nine 6-inch cherry tomato plants were selected to be as uniform as possible. Each member of Group 1 was spotted over a 2 square centimeter area of the second leaf from the top of the plant. Fifty microliters of solution was applied. The 2 square centimeters had 64,000 corrected counts per minute, or in other words 5 microcuries of $Fe^{59}$ isotope. Twenty microvolts energy sound at a frequency of between 4.7 and 6 kilohertz was applied for 15 minutes following the spotting. Group 2 was treated identically to Group 1 except the sound was not applied. Group 3 was treated the same as Group 1 except they did not receive either chemical or sound treatments. The terminal leaf, opposite leaf, stem above point of application and stem below point of application were collected on all plants 24 hours post application. Corrected counts per minute per mg. were as follows:

| | Group 1 | Group 2 | Group 3 |
|---|---|---|---|
| Terminal Leaf | $0.3 \pm 0.2$ | $.67 \pm .29$ | $0.2 \pm .16$ |
| Opposite Leaf | $.17 \pm .12$ | $.47 \pm .46$ | $.23 \pm .06$ |
| Stem Above | $2.47 \pm 0.4$ | $.40 \pm 0.1$ | $0.6 \pm .18$ |
| Stem Below | $2.5 \pm .17$ | $1.13 \pm .42$ | $3.5 \pm .22$ |

EXAMPLE XIII

The present invention was carried out using a post emergent herbicide in combination with the application of sound on grassy weeds. The herbicide was Hoegrass TM produced by Hertz Chemical, Ltd. The active ingredient was diclofop methyl. Twenty liters of concentrate containing 190 grams per liter active ingredient was diluted to 530 gallons by the addition of water. This dilution contained only 25 percent of the usual recommended active ingredient. The diluted solution was applied by a drawn boom-type sprayer at a rate of 10 gallons per acre while sound was applied at a frequency of between 4 and 6 kilohertz and at a transmitted volume of 115 decibels. Although the herbicide, together with sound, was applied at a level of only 25 percent of normal recommended application, the effect on eradicating the grassy weeds, primarily wild oats, was essentially the same as full application using no sound.

EXAMPLE XIV

The present invention was carried out using a post emergent herbicide (Hoe-grass 2 TM by Hertz Chemical, Ltd.) in combination with sound on broadleaf weeds and grassy weeds. This herbicide included diclofop methyl and bromoxynil having active ingredients of 310 grams per liter. Twenty liters of the herbicide concentrate were diluted with water to 540 gallons which is 25 percent of the usual recommended application concentration. The herbicide was applied at a rate of 10 gallons per acre while applying sound at 4 to 6 kilohertz and at a volume of about 115 decibels for at least 15 minutes. Satisfactory herbicidal results were obtained on a cultivated field having substantial broadleaf and grassy weed infestation.

EXAMPLE XV

The present invention was carried out using Saber TM herbicide. Saber is a 1:1 mixture of Bromoxynil and META. The concentrate had 720 grams active ingredient per liter. Twenty gallons of Saber were diluted with water to 540 gallons and applied at the rate of 10 gallons per acre. This application is 25 percent of the recommended dosage. The application was accompanied with sound as described in Example XIV. The application satisfactorily eradicated the growth of weeds in a cultivated field having a mixture of common weeds.

EXAMPLE XVI

The present invention was carried out as described in Example XIV, however using META Extamene TM. The active ingredient is META amine. The concentrate had 500 grams active ingredient per liter. Similar results were obtained.

EXAMPLE XVII

The present invention was carried out using Target TM. The active ingredient was a mixture of decamba, mecoprat and MCTA. The concentrate had 400 grams active ingredient per liter. Dilution and application was as described in Example XV. Similar results were obtained.

EXAMPLE XVIII

The present invention may be carried out using Ortho TM Crab Grass killer. A concentrate having by weight 8 percent octyl ammonium methane arsonate and 8 percent dodecyl ammonium methanearsonate. One tablespoon may be diluted with water to one gallon and applied to 200 square feet of lawn to effectively kill crab grass. Sound is applied at a frequency of between 4 and 6 kilohertz for at least 30 seconds following application of the solution.

EXAMPLE XIX

The present invention may be carried out using Ortho Weed-B-Gon TM lawn weed killer. The active ingredients are 21.4 percent butoxy propyl esters of 2,4-dichlorophenoxyacetic acid and 10 percent 2(2,4,5-trichlorophenoxy) propanoic acid by weight in the concentrate. One teaspoon of the concentrate may be diluted to one gallon with water. The solution may be applied by spraying on 167 square feet of lawn infested with such weeds as buckhorn plantain, Canada thistle, common burdock, common plantain, curly dock, dandelion, dichondra, ground hog, lawn pennywort, lippia, morningglory, wild garlic and wild onions. Sound is applied as described in Example XVIII. Satisfactory results are obtained.

EXAMPLE XX

A procedure was carried out to compare the present invention utilizing the combination of sound and herbicide with processing including only treatment with herbicide. A composition was first prepared including 4 pints of Basagran TM herbicide and 150 gallons of water. Five gallons of 28% liquid nitrogen fertilizer and one gallon of molasses were added. The combination was thoroughly mixed and was applied to a plot infested with pigweed, velvetleaf, lambsquarters and cockleburr. The application was at the rate of .66 pints per acre. This is approximately one-half of the recommended minimum rate for this herbicide. Basagran TM is a postemergent herbicide using 3-isopropyl-1H-2,1,3-benzothiadiazin-(4)3H-one,2,2-dioxide. This is an herbicide originated by BASF of West Germany. The molasses and the liquid nitrogen were included to serve as a surfactant. The application was made using a tractor-mounted sprayer with a fan tip nozzle. The boom height was 30 inches above the canopy. The composition was applied at 6:00 p.m. at a temperature of 80° F. The humidity was in the mid-70's and there were overcast skies. The tractor moved at a speed of 5.5 mph during the application. This application did not include the use of sound.

A second strip of the same weed infested field was treated 23 hours later, all conditions being the same except that a sound unit was used throughout the application of the herbicide composition at a frequency of 4 to 6 kilohertz and a volume of 115 decibels. The sound unit was activated five minutes prior to entering the field. The chemical Basagran TM herbicide was applied in an identical manner as on the first piece of land discussed above. The tractor was driven back through this strip of land with the sound unit on, but without additional spraying of the chemical composition. The following indicates the percent of eradication for each of the four weeds contained in the field:

|  | treated with herbicide (no sound) | Treated With Herbicide and Sound |
| --- | --- | --- |
| Pigweed | 6.6 | 45.0 |
| Velvetleaf | 1.6 | 81.6 |
| Lambsquarter | 0.0 | 26.6 |
| Cockleburr | 10.0 | 76.6 |

EXAMPLE XXI

Two test areas were selected, approximately one-quarter mile apart and having weed infestation approximately equal. One test area was sprayed while simultaneously applying sound at a frequency of between 4 and 6 kilohertz and a volume of about 115 decibels. The other strip was only sprayed. In both instances, the composition was the same as the previous Example; however, the application rate was at 1.5 pints of Basagran TM per acre. The strip included 90% burndown of rough pigweed when sound was used and only 65% when no sound was used.

EXAMPLE XXII

A similar test as the preceding Example was carried out using Poast grass herbicide added to the previously described Basagran TM mixture. The combination was applied with the Poast herbicide at a rate of 0.5 pints per acre and the Basagran TM at a rate of 1.25 pints per acre. The combination was applied to giant foxtail which was present in a navy bean field. The foxtail was about 6-8 inches above the navy bean canopy, and was approximately 20 inches tall overall. One hour later, an adjoining strip was sprayed with the same composition and at the same application rate. The results indicated 85% kill on the sound treated strip and only 50% kill on the adjoining strip which was only sprayed with the chemical composition.

EXAMPLE XXIII

A first area of a soybean field was treated with the composition set forth in Example XX. The application rate was 1 pint per acre. No sound application was made. The strip was one-quarter mile in length and fourteen rows in width. Two hours later an adjoining fourteen rows of soybeans were treated at the rate of 0.5 pints per acre. This was carried out by increasing the rate of travel of the tractor to provide the desired application rate of chemical. In this instance, sound was applied at a frequency of between 4 and 6 kilohertz and a volume of approximately 115 decibels. No discernable difference was noted between the two strips of beans. In both instances, about 70% eradication of velvetleaf was obtained; 80% kill of cockleburr, thus showing that one can significantly reduce the herbicide usage, providing one uses the sound application of the present invention.

While various specific embodiments and suggested herbicides have been set forth in this application, it is to be recognized that any herbicide that is taken up by the plant in controlling infestation may be used in the present invention, providing the sound application of the present invention is likewise used.

What is claimed is:

1. A process for treating plants comprising applying to said plants a growth eradicating solution of the herbicide 2,4-D to wet the leaves of said plants and applying high frequency sound waves to facilitate reception of said growth eradicating solution into said plants.

2. The process of claim 1 wherein said solution is a herbicide effective on broadleaf plants.

3. The process of claim 2 wherein said solution comprises an aqueous solution of 2,4-D.

4. The process of claim 1 wherein the sound frequency is between about 4 and 6 kilohertz.

5. The process of claim 4 wherein said sound waves are of a frequency of between about 4.7 and 5.3 kilohertz.

6. The process of claim 4 wherein said sound waves are applied at a volume of at least 115 decibels.

7. The process of claim 6 wherein the sound waves are applied for at least 30 seconds while the herbicide is present on the plant.

8. A process of treating plants to inhibit growth, said process comprising applying to said plants a growth eradicating composition of the herbicide 2,4-D, said composition being suitable for uptake by said plants to inhibit plant growth and while said composition is in uptake contact with said plant applying to said plants and composition high frequency sound waves to facilitate reception of said growth eradicating composition into said plants.

9. The process of claim 8 wherein said sound is applied at a frequency of between 4 and 6 kilohertz and for a time period of at least 30 seconds.

10. The process of claim 9 wherein said herbicide is an aqueous solution.

11. The process of claim 10 wherein said plants are broadleaf plants and wherein said herbicide is effective for the growth eradication of broadleaf plants.

12. The process of claim 10 wherein said plants are woody plants and wherein said herbicide is effective for the growth eradication of woody plants.

13. The process of claim 10 wherein said plants are grass and wherein said herbicide is effective for the growth eradication of grasses.

14. A process of treating plants to eradicate growth, said process comprising applying to said plants a growth eradicating composition of the herbicide 2,4-D, said composition being in a form suitable for uptake by said plants to eradicate plant growth and while said composition is in uptake contact with said plant applying to said plants and composition high frequency sound waves to force osmosis of said growth eradicating composition into said plants and wherein said sound is applied at a frequency of between 4 and 6 kilohertz and for a time period of at least 30 seconds.

15. The process of claim 14 wherein said plants are a member selected from the group consisting of Canadian thistle, quackgrass, yellow nutsedge, bluegrass, sowthistle, field bindweed, leafy spurge, common milkweed, wirestem muhly, perennial buttercups, germander, bull thistle, cocklebur, chickweed, goldenrod, pigweed, mustards, burdoch, button weed, wild sunflowers, ash, wild blackberry, hawthorne, oak, ivy, sumac, maple, willow, chokeberry, poison ivy, mesquite, brambles, wild grape, honeysuckle, alder, pine, fir, spruce, rag weed, pokeberry, yucca, smartweed, clovers, knotweed, shepherds purse, crabgrass, foxtail, coffeeweed, teaweed, kochia, velvetleaf, cockles, knapweed, dock, gooseweed, toadflax, johnsongrass, dandelions, sandbur, groundcherry, morningglory, beggarweed, annual gluegrass, fiddleneck, tarweed, speedwell, and shattercrane.

* * * * *